United States Patent [19]

Tomcufcik et al.

[11] 4,421,753
[45] Dec. 20, 1983

[54] 1-(5-AMINO-4H-1,2,4-TRIAZOL-3-YL)-4-SUBSTITUTED-PIPERAZINES

[75] Inventors: Andrew S. Tomcufcik, Old Tappan, N.J.; Walter E. Meyer, Suffern; John P. Dusza, Nanuet, both of N.Y.

[73] Assignee: American Cyanamid Company, Stamford, Conn.

[21] Appl. No.: 360,864

[22] Filed: Mar. 22, 1982

Related U.S. Application Data

[63] Continuation-in-part of Ser. No. 339,361, Jan. 15, 1982, abandoned.

[51] Int. Cl.$^3$ .................... C07D 417/14; A61K 31/50
[52] U.S. Cl. .................................... 424/250; 544/366; 544/363; 544/392
[58] Field of Search ................. 544/366, 363; 424/250

[56] References Cited

U.S. PATENT DOCUMENTS 3,631,043 12/1971 Regnier et al. ...................... 544/366
3,944,551  3/1976 Regnier et al. ...................... 544/363
4,177,272 12/1979 Regnier et al. ...................... 544/366

Primary Examiner—Donald G. Daus
Assistant Examiner—S. A. Gibson
Attorney, Agent, or Firm—Edward A. Conroy, Jr.

[57] ABSTRACT

This disclosure describes novel 1-(5-amino-4H-1,2,4-triazol-3-yl)-4-substituted-piperazines which are useful as hypotensive agents in mammals.

30 Claims, No Drawings

1-(5-AMINO-4H-1,2,4-TRIAZOL-3-YL)-4-SUBSTITUTED-PIPERAZINES

CROSS REFERENCE TO RELATED APPLICATION

This application is a continuation-in-part of our copending application Ser. No. 339,361, filed Jan. 15, 1982 now abandoned.

BRIEF SUMMARY OF THE INVENTION

This invention relates to new organic compounds and, more particularly, is concerned with novel 1-(5-amino-4H-1,2,4-triazol-3-yl)-4-substituted-piperazines which may be represented by the following structural formula:

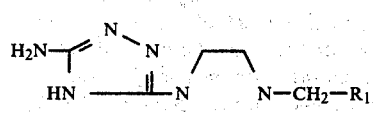
(I)

wherein $R_1$ is alkyl having up to 3 carbon atoms, cycloalkyl having from 3 to 6 carbon atoms, allyl, styryl, benzyl, β-phenethyl, β-phenoxyethyl, 3,4,5-trimethoxyphenyl, 2-furyl, 2-quinolyl, 2-phenyl-2H-1,2,3-triazol-4-yl or a moiety of the formula:

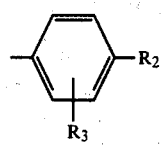

wherein $R_2$ is hydrogen, alkyl having up to 4 carbon atoms, fluoro, chloro, bromo, cyano, amino, or dimethylamino and $R_3$ is hydrogen, methyl, fluoro, chloro, bromo or nitro. The invention also includes novel compositions of matter containing the above-defined compounds useful as hypotensive agents and the method of meliorating hypertension in mammals therewith.

In general formula (I), the hydrogen is placed on the nitrogen in the 4-position as a matter of convenience. It is obvious that the hydrogen could also be found on the nitrogens in the 1-position or 2-position, as follows:

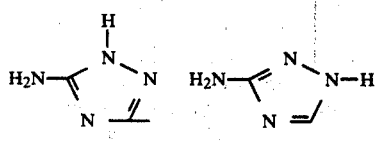

All three tautomeric structures are included within the scope of the present invention.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition salts with a variety of organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The novel compounds of the present invention may be readily prepared by the following reaction scheme:

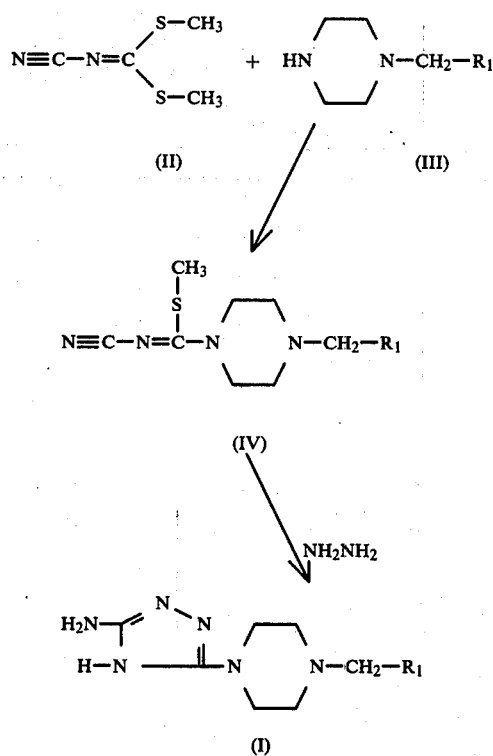

In accordance with the above reaction sequence, dimethyl cyanodithioiminocarbonate (II) and a piperazine (III) where $R_1$ is as described above are refluxed in acetonitrile, ethanol or a similar solvent for 4–18 hours, giving the N-cyano-4-substituted-1-piperazinecarboximidothioic acid, methyl ester (IV) which is then refluxed with hydrazine hydrate in a solvent such as acetonitrile or ethanol, giving the products (I) of this invention.

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, New York having an average mean arterial blood pressure of 170±1.5 mm. of mercury are used in the test. One to 3 rats are used per test compound. A rat is dosed by gavage with a test compound, suspended in 2% pre-boiled starch at a concentration of 50 mg./ml., at a dose of 100 mg./kg. of body weight or less, with 0.9% sodium chloride loading at a dose of 25 ml./kg. of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary. Based on the data obtained and using the three-stage "sequential probability ratio test" statistical method, the criteria for activity or retest are as follows:

If the blood pressure in the first rat is $\leq 116$ mm. mercury the compound is considered active. If the blood pressure is between 117 and 146 mm., a second rat is used. If the average blood pressure of the first and second rats is $\leq 122$ mm. the compound is considered active. If the average blood pressure is between 123 and 137 mm., a third rat is used. If the average blood pressure of the three rats is $\leq 128$ mm. the compound is considered active. The results of this test on representative compounds of the present invention appear below in Table I.

TABLE I

| Compound | Result |
| --- | --- |
| 1-(5-amino-4H-1,2,4-triazol-3-yl)-4-benzyl-piperazine | Active |
| 1-(5-Amino-4H-1,2,4-triazol-3-yl)-4-(p-chloro-α-phenylbenzyl)-piperazine | Active |
| 1-(5-Amino-4H-1,2,4-triazol-3-yl)-4-methyl-piperazine | Active |
| 1-(5-Amino-4H-1,2,4-triazol-3-yl)-4-(p-methyl-benzyl)piperazine | Active |
| 1-(5-Amino-4H-1,2,4-triazol-3-yl)-4-(p-fluoro-benzyl)piperazine | Active |
| 1-(5-Amino-4H-1,2,4-triazol-3-yl)-4-(β-phen-ethyl)piperazine | Active |
| 1-Allyl-4-(5-amino-4H-1,2,4-triazol-3-yl)-piperazine | Active |
| 1-(5-Amino-4H-1,2,4-triazol-3-yl)-4-(cyclo-hexylmethyl)-piperazine | Active |
| 1-(5-Amino-4H-1,2,4-triazol-3-yl)-4-(o-fluoro-benzyl)piperazine | Active |
| α-[4-(5-Amino-4H-1,2,4-triazol-3-yl)-1-pipera-zinyl]-p-tolunitrile | Active |
| 2-[[4-(5-Amino-4H-1,2,4-triazol-3-yl)-1-piperazinyl]methyl]-quinoline | Active |
| 1-(5-Amino-4H-1,2,4-triazol-3-yl)-4-furfuryl-piperazine | Active |
| 1-(5-Amino-4H-1,2,4-triazol-3-yl)-4-(p-dimethylaminobenzyl)-piperazine | Active |
| 1-(5-Amino-4H-1,2,4-triazol-3-yl)-4-(3-phenyl-propyl)-piperazine | Active |
| 1-(5-Amino-4H-1,2,4-triazol-3-yl)-4-cinnamyl-piperazine | Active |
| 1-(5-Amino-4H-1,2,4-triazol-3-yl)-4-(3-bromo-p-dimethylaminobenzyl)-piperazine | Active |
| 1-(5-Amino-4H-1,2,4-triazol-3-yl)-4-(m-chloro-benzyl)piperazine | Active |
| 1-(5-Amino-4H-1,2,4-triazol-3-yl)-4-(2-chloro-4-dimethylaminobenzyl)-piperazine | Active |
| 1-(p-Aminobenzyl)-4-(5-amino-4H-1,2,4-triazol-3-yl)-piperazine | Active |
| 1-(5-Amino-4H-1,2,4-triazol-3-yl)-4-(o-methyl-benzyl)piperazine | Active |
| 1-(5-Amino-4H-1,2,4-triazol-3-yl)-4-cyclo-pentyl-piperazine | Active |
| 1-(5-Amino-4H-1,2,4-triazol-3-yl)-4-(3,4,5-trimethoxybenzyl)-piperazine | Active |
| 1-(5-Amino-4H-1,2,4-triazol-3-yl)-4-(m-methyl-benzyl)piperazine | Active |
| 1-(5-Amino-4H-1,2,4-triazol-3-yl)-4-[(2-phenyl-2H-1,2,3-triazol-4-yl)methyl]-piperazine | Active |
| 1-(5-Amino-4H-1,2,4-triazol-3-yl)-4-(p-butyl-benzyl)piperazine | Active |
| 1-(5-Amino-4H-1,2,4-triazol-3-yl)-4-(p-tert.-butylbenzyl)piperazine | Active |

The active compounds of the present invention are effective hypotensive agents in warm-blooded animals when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound is such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

1-p-Methylbenzyl)piperazine

A mixture of 31.6 g. of ethyl 1-piperazinecarboxylate, 25 g. of potassium carbonate and 250 ml. of dry tetrahydrofuran was cooled and stirred. A 16 g. portion of p-toluoyl chloride was added and the mixture stirred for 18 hours. The reaction mixture was filtered, washed with tetrahydrofuran and evaporated to a syrup. This syrup was extracted with two 500 ml. portions of chloroform and saturated sodium bicarbonate. The extracts were dried, filtered and evaporated, giving 27.6 g. of 4-p-toluoyl-1-piperazinecarboxylic acid, ethyl ester as a pale yellow syrup.

A mixture of 25.4 g. of the above syrup in 200 ml. of dry tetrahydrofuran was stirred under nitrogen as 100 ml. of a 1 M solution of diborane in tetrahydrofuran was added over 15 minutes. The mixture was allowed to stand 18 hours, then 150 ml. of 12 N hydrochloric acid was added. The tetrahydrofuran was removed by distillation and then the mixture was refluxed for 4 hours, evaporated and 10 N sodium hydroxide is added to pH>7. The mixture was extracted with chloroform. The extracts were dried and evaporated to an oil which may be crystallized from n-hexane, giving 1-(p-methylbenzyl)piperazine.

EXAMPLE 2

α-(1-Piperazinyl)-p-tolunitrile

A mixture of 13.1 g. of p-cyanobenzaldehyde and 15 ml. of piperazine-1-carboxaldehyde was heated to 100° C. Over 10 minutes, 6 g. of 99% formic acid were added. The mixture was heated for 3 hours, then 200 ml. of 3.6 N hydrochloric acid in ethanol were added and the mixture was refluxed for 4 hours. The solid was collected, washed with ether and suspended in water. 10 N Sodium hydroxide extracted with three 100 ml. portions of chloroform and the combined extracts were evaporated. The residue was suspended in a mixture of 6 N hydrochloric acid and chloroform and filtered. The filtrate was adjusted to pH>7 with 10 N sodium hydroxide, extracted with chloroform, and the extract dried and evaporated to an oil which was distilled, giving α-(1-piperazinyl)-p-tolunitrile as a colorless liquid, b.p. 207°–209° C. (15 mm.).

EXAMPLE 3

2-(1-Piperazinylmethyl)quinoline, trihydrochloride

A mixture of 21.4 g. of quinolylmethyl chloride hydrochloride, 18 g. of ethyl 1-piperazinecarboxylate, 20 g. of sodium bicarbonate and one gram of potassium iodide in 500 ml. of ethanol was stirred at reflux for 18 hours, cooled and then filtered. The filtrate was evaporated in vacuo to an oil. The oil was dissolved in 250 ml. of acetone, treated with charcoal, filtered and 55 ml. of 3.85 N hydrochloric acid in ethanol were added. A 250 ml. of portion of acetone was added, the solid was collected, washed with 100 ml. of acetone and 200 ml. of ether and dried giving 32 g. of 4-(2-quinolylmethyl)-1-piperazinecarboxylic acid, ethyl ester, hydrochloride.

A 27 g. portion of this ester was dissolved in 250 ml. of concentrated hydrochloric acid and refluxed overnight. A 200 ml. portion of methyl cellosolve was added and the solution was evaporated to turbidity, then filtered. The filtrate was evaporated to dryness in vacuo and the residue was taken up in 300 ml. of boiling ethanol and 35 ml. of water. This solution was filtered while hot, cooled to −10° C. and 200 ml. of acetone were added. The solid was collected, washed with 200 ml. of acetone and dried, giving 18 g. of 2-(1-piperazinylmethyl)quinoline, trihydrochloride.

EXAMPLE 4

1-(p-n-Butylbenzyl)-piperazine

A 26.4 g. portion of 1-benzylpiperazine, 25 g. of potassium carbonate and 200 ml. of dry tetrahydrofuran were stirred and cooled. A 31.5 g. portion of 4-n-butyl benzoyl chloride and 100 ml. of tetrahydrofuran were added and the mixture stirred 18 hours. A 100 ml. portion of 1 N sodium hydroxide was added and the mixture stirred for one hour. The phases were separated. The aqueous phase was extracted with 100 ml. of chloroform. The extract was combined with the tetrahydrofuran layer, dried and evaporated to an oil. This oil was suspended in a mixture of 100 ml. of glacial acetic acid and 10 ml. of water, 4 g. of 10% palladium on carbon catalyst were added and the mixture reduced. The reaction mixture was filtered. The filtrate was washed with ethanol, evaporated to a syrup and triturated with ether, giving 17.5 g. of colorless crystals. A 17.0 g. portion of these crystals were dissolved in water and 10 N sodium hydroxide added to a pH>10. This mixture was extracted with two 200 ml. portions of chloroform. The extracts were combined, dried and evaporated to give 12.3 g. of 1-(p-n-butylbenzoyl)-piperazine as a viscous syrup. This was dissolved in 250 ml. of dry tetrahydrofuran, 2 g. of lithium aluminum hydride was added, and the mixture was stirred and refluxed for 20 hours. The reaction mixture was cooled, treated with aqueous sodium carbonate solution, and the tetrahydrofuran was removed in vacuo. The aqueous solution was extracted with chloroform followed by concentration of the extract in vacuo giving the title compound as a colorless oil, b.p. 127°–130° C./0.05 mm.

EXAMPLES 5–26

Other piperazine starting materials for the required reaction sequence prepared by essentially following one of the procedures described in Examples 1–3, using an appropriate piperazine such as 1-formylpiperazine, 1-benzylpiperazine, or ethyl 1-piperazinecarboxylate and the starting materials listed in Table II.

TABLE II

| Example | Starting Material | Procedure of Example | Piperazine |
|---|---|---|---|
| 5 | p-fluorobenzoyl chloride | 1 | 1-(p-fluorobenzyl)-piperazine |
| 6 | β-phenylethyl bromide | 1 | 1-(β-phenethyl)piperazine |
| 7 | allyl chloride | 1 | 1-allyl-piperazine |
| 8 | cyclohexanecarboxaldehyde | 1 | 1-(cyclohexylmethyl)-piperazine |
| 9 | o-fluorobenzoyl chloride | 1 | 1-(o-fluorobenzyl)-piperazine |
| 10 | furfural | 2 | 1-furfuryl-piperazine |
| 11 | 4-dimethylaminobenzaldehyde | 2 | 1-(p-dimethylaminobenzyl)piperazine |
| 12 | 3-phenylpropyl bromide | 3 | 1-(3-phenylpropyl)-piperazine |
| 13 | 3-phenylallyl bromide | 1 | 1-cinnamyl-piperazine |
| 14 | o-bromo-p-dimethylaminobenzaldehyde | 2 | 1-(o-bromo-p-dimethylaminobenzyl)piperazine |
| 15 | m-chlorobenzyl chloride | 1 | 1-(m-chlorobenzyl)-piperazine |
| 16 | m-chloro-p-dimethylaminobenzaldehyde | 2 | 1-(m-chloro-p-dimethylaminobenzyl)piperazine |
| 17 | 4-acetamidobenzaldehyde | 2 | 1-(p-aminobenzyl)piperazine |
| 18 | o-methylbenzyl bromide | 1 | 1-(o-methylbenzyl)-piperazine |
| 19 | cyclopentyl bromide | 1 | 1-cyclopentyl-piperazine |
| 20 | 3,4,5-trimethoxybenzyl chloride | 1 | 1-(3,4,5-trimethoxybenzyl)piperazine |
| 21 | m-methylbenzyl bromide | 1 | 1-(m-methylbenzyl)piperazine |
| 22 | 1-(2-phenyl-2H-1,2,3-triazol-4-yl)methyl bromide | 1 | 1-[(2-phenyl-2H-1,2,3-triazol-4-yl)methyl]-piperazine |
| 23 | p-(tert.-butyl)-benzyl chloride | 1 | 1-(p-tert.-butylbenzyl)-piperazine |
| 24 | 3-phenoxypropyl bromide | 1 | 1-(3-phenoxypropyl)-piperazine |
| 25 | o-nitrobenzyl bromide | 1 | 1-(o-nitrobenzyl)piperazine |
| 26 | chloromethylcyclopropane | 3 | 1-cyclopropylmethyl-piperazine |

EXAMPLE 27

N-Cyano-4-(p-fluorobenzyl)-1-piperazinecarboximidothioic acid, methyl ester

A 28.7 g. (0.1 mole) portion of N-(p-fluorobenzyl)piperazine was dissolved in 25 ml. of ethanol and then added dropwise over 30 minutes to a stirred solution of 14.6 g. (0.1 mole) of dimethyl cyanodithioiminocarbonate in 200 ml. of ethanol. The mixture was refluxed for 6 hours, the evolved gas being led through a sodium hypochlorite trap. The mixture was then evaporated to a syrup.

Following the procedure of Example 27, using equimolar portions of dimethyl cyanodithioiminocarbonate and other piperazine derivatives, the intermediates of Examples 28–55 presented in Table III were prepared. These intermediates were recovered as oils or in some cases were crystallized from a mixture of an alcohol and hexane.

TABLE III

| Example | Piperazine | Intermediate | M.P. °C. |
|---|---|---|---|
| 28 | N—methylpiperazine | N—cyano-4-methyl-1-piperazinecarboximidothioic acid, methyl ester | 61–63 |
| 29 | 1-(p-methylbenzyl)-piperazine | N—cyano-4-(p-methylbenzyl)-1-piperazinecarboximidothioic acid, methyl ester | |
| 30 | 1-(p-fluorobenzyl)-piperazine | N—cyano-4-(p-fluorobenzyl)-1-piperazinecarboximidothioic acid, methyl ester | |
| 31 | 1-(β-phenethyl)piperazine | N—cyano-4-(β-phenethyl)-1-piperazinecarboximidothioic acid, methyl ester | |
| 32 | 1-allylpiperazine | 4-allyl-N—cyano-1-piperazinecarboximidothioic acid, methyl ester | 75–76 |
| 33 | 1-(cyclohexylmethyl)-1-piperazine hydrobromide | N—cyano-4-cyclohexylmethyl-1--piperazinecarboximidothioic acid, methyl ester | |
| 34 | 1-(o-fluorobenzyl)-piperazine | N—cyano-4-(o-fluorobenzyl)-1-piperazinecarboximidothioic acid, methyl ester | |
| 35 | α-(1-piperazinyl)-p-tolunitrile | N—cyano-4-(p-cyanobenzyl)-1-piperazinecarboximidothioic acid, methyl ester | |
| 36 | 2-(1-piperazinylmethyl)quinoline | N—cyano-4-quinolylmethyl-1-piperazinecarboximidothioic acid, methyl ester | |
| 37 | 1-furfuryl-piperazine | N—cyano-4-furfuryl-1-piperazinecarboximidothioic acid, methyl ester | |
| 38 | 1-(p-dimethylaminobenzyl)piperazine | N—cyano-4-(p-dimethylaminobenzyl)-1-piperazinecarboximidothioic acid, methyl ester | |
| 39 | 1-(3-phenylpropyl)-piperazine | N—cyano-4-(3-phenylpropyl)-1-piperazinecarboximidothioic acid, methyl ester | |
| 40 | 1-cinnamyl-piperazine dihydrochloride | N—cyano-4-(3-phenylallyl)-1--piperazinecarboximidothioic acid, methyl ester | |

TABLE III-continued

| Example | Piperazine | Intermediate | M.P. °C. |
|---|---|---|---|
| 41 | 1-(o-bromo-p-dimethyl-aminobenzyl)piperazine | N—cyano-4-(o-bromo-p-dimethylaminobenzyl)-1-piperazinecarboximidothioic acid, methyl ester | |
| 42 | 1-(m-chlorobenzyl)-piperazine | N—cyano-4-(m-chlorobenzyl)-1-piperazinecarboximidothioic acid, methyl ester | |
| 43 | 1-(m-chloro-p-dimethylaminobenzyl)piperazine | N—cyano-4-(m-chloro-p-dimethylaminobenzyl)-1-piperazinecarboximidothioic acid, methyl ester | |
| 44 | 1-(p-aminobenzyl)-piperazine | N—cyano-4-(p-aminobenzyl)-1-piperazinecarboximidothioic acid, methyl ester | |
| 45 | 1-(o-methylbenzyl)-piperazine | N—cyano-4-(o-methylbenzyl)-1-piperazinecarboximidothioic acid, methyl ester | |
| 46 | 1-cyclopentylpiperazine | N—cyano-4-cyclopentyl-1-piperazinecarboximidothioic acid, methyl ester | |
| 47 | 1-(3,4,5-trimethoxybenzyl)piperazine | N—cyano-4-(3,4,5-trimethoxybenzyl)-1-piperazinecarboximidothioic acid, methyl ester | |
| 48 | 1-(m-methylbenzyl)-piperazine | N—cyano-4-(m-methylbenzyl)-1-piperazinecarboximidothioic acid, methyl ester | |
| 49 | 1-[(2-phenyl-2H-1,2,3-triazol-4-yl)methyl]-piperazine | N—cyano-4-[(2-phenyl-2H-1,2,3-triazol-4-yl)methyl]-1-piperazinecarboximidothioic acid, methyl ester | |
| 50 | 1-(p-n-butylbenzyl)piperazine | N—cyano-4-(p-n-butylbenzyl)-1-piperazinecarboximidothioic acid, methyl ester. | |
| 51 | 1-(p-tert.-butylbenzyl)piperazine | N—cyano-4-(p-tert.-butylbenzyl)-1-piperazinecarboximidothioic acid, methyl ester | |
| 52 | 1-(3-phenoxypropyl)-piperazine | N—cyano-4-(3-phenoxypropyl)-1-piperazinecarboximidothioic acid, methyl ester | |
| 53 | 1-(o-nitrobenzyl)-piperazine | N—cyano-4-(o-nitrobenzyl)-1-piperazinecarboximidothioic acid, methyl ester | |
| 54 | 1-(cyclopropylmethyl)-piperazine | N—cyano-4-cyclopropylmethyl-1-piperazinecarboximidothioic acid, methyl ester | |
| 55 | 1-benzylpiperazine | N—cyano-4-benzyl-1-piperazinecarboximidothioic acid, methyl ester | |

EXAMPLE 56

1-(5-Amino-4H-1,2,4-triazol-3-yl)-4-(p-fluorobenzyl)-piperazine

The entire portion (0.1 mole) of N-cyano-4-(p-fluorobenzyl)-1-piperazinecarboximidothioic acid, methyl ester, prepared as an oil (Example 27) was dissolved in 150 ml. of ethanol and 5.5 ml. (0.11 mole) of hydrazine hydrate were added. The mixture was refluxed for 6 hours and then evaporated to a solid residue which as crystallized from 200 ml. of ethanol, giving 21 g. of the desired product as colorless crystals, m.p. 213°–216° C. (dec.).

Following the procedure of Example 56, but using the intermediates of Examples 28–55, the products of Examples 57–84, presented in Table IV were obtained.

TABLE IV

| Example | Intermediate Example No. | Product | M.P. °C. |
|---|---|---|---|
| 57 | 28 | 1-(5-amino-4H-1,2,4-triazol-3-yl)-4-methyl-piperazine | 51-53 |
| 58 | 29 | 1-(5-amino-4H-1,2,4-triazol-3-yl)-4-(p-methylbenzyl)-piperazine | 153-154 |
| 59 | 30 | 1-(5-amino-4H-1,2,4-triazol-3-yl)-4-(p-fluorobenzyl)-piperazine | 177-179 |
| 60 | 31 | 1-(5-amino-4H-1,2,4-triazol-3-yl)-4-phenethyl-piperazine | 136-138 |
| 61 | 32 | 1-allyl-4-(5-amino-4H-1,2,4-triazol-3-yl)-piperazine | 88-91 |
| 62 | 33 | 1-(5-amino-4H-triazol-3-yl)-4-(cyclohexylmethyl)-piperazine | 175-176 |
| 63 | 34 | 1-(5-amino-4H-1,2,4-triazol-3-yl)-4-(o-fluorobenzyl)-piperazine | 92-95 |
| 64 | 35 | α-[4-(5-amino-4H-1,2,4-triazol-3-yl)-1-piperazinyl]-p-tolunitrile | 213-215 |
| 65 | 36 | 2-[[4-(5-amino-4H-1,2,4-triazol-3-yl)-1-piperazinyl]methyl]-quinoline | 149-150 |
| 66 | 37 | 1-(5-amino-4H-1,2,4-triazol-3-yl)-4-furfuryl-piperazine | 196-197 |
| 67 | 38 | 1-(5-amino-4H-1,2,4-triazol-3-yl)-4-(p-dimethylaminobenzyl)-piperazine | 161-163 |
| 68 | 39 | 1-(5-amino-4H-1,2,4-triazol-3-yl)-4-(3-phenylpropyl)-piperazine | 91-93 |

TABLE IV-continued

| Example | Intermediate Example No. | Product | M.P. °C. |
|---|---|---|---|
| 69 | 40 | 1-(5-amino-4H-1,2,4-triazol-3-yl)-4-cinnamyl-piperazine | 119–121 |
| 70 | 41 | 1-(5-amino-4H-1,2,4-triazol-3-yl)-4-(3-bromo-p-dimethylaminobenzyl)-piperazine | 189–190 |
| 71 | 42 | 1-(5-amino-4H-1,2,4-triazol-3-yl)-4-(m-chlorobenzyl)-piperazine | 195–196 |
| 72 | 43 | 1-(5-amino-4H-1,2,4-triazol-3-yl)-4-(o-chloro-p-dimethylaminobenzyl)-piperazine | 180–181 |
| 73 | 44 | 1-(p-aminobenzyl)-4-(5-amino-4H-1,2,4-triazol-3-yl)-piperazine | 203–205 |
| 74 | 45 | 1-(5-amino-4H-1,2,4-triazol-3-yl)-4-(o-methylbenzyl)-piperazine | 169–170 |
| 75 | 46 | 1-(5-amino-4H-1,2,4-triazol-3-yl)-4-cyclopentyl-piperazine | 185–186 |
| 76 | 47 | 1-(5-amino-4H-1,2,4-triazol-3-yl)-4-(3,4,5-trimethoxybenzyl)-piperazine | 223–225 |
| 77 | 48 | 1-(5-amino-4H-1,2,4-triazol-3-yl)-4-(m-methylbenzyl)-piperazine | 191–193 |
| 78 | 49 | 1-(5-amino-4H-1,2,4-triazol-3-yl)-4-[(2-phenyl-2H-1,2,3-triazol-4-yl)-methyl]-piperazine | 194–196 |
| 79 | 50 | 1-(5-amino-4H-1,2,4-triazol-3-yl)-4-(p-butylbenzyl)-piperazine | 147–149 |
| 80 | 51 | 1-(5-amino-4H-1,2,4-triazol-3-yl)-4-(p-tert.-butylbenzyl)-piperazine | 102–111 |
| 81 | 52 | 1-(5-amino-4H-1,2,4-triazol-3-yl)-4-(3-phenoxypropyl)-piperazine | 151–153 |
| 82 | 53 | 1-(5-amino-4H-1,2,4-triazol-3-yl)-4-(o-nitrobenzyl)-piperazine | 106–110 |
| 83 | 54 | 1-(5-amino-4H-1,2,4-triazol-3-yl)-4-(cyclopropylmethyl)-piperazine | 141–142 |
| 84 | 55 | 1-(5-amino-4H-1,2,4-triazol-3-yl)-4-benzyl-piperazine | 160–161 |

We claim:

1. A compound selected from the group consisting of those of the formula:

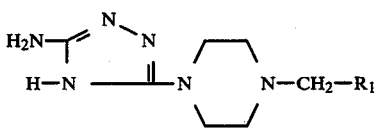

wherein $R_1$ is selected from the group consisting of alkyl having up to 3 carbon atoms, cycloalkyl having from 3 to 6 carbon atoms, allyl, benzyl, β-phenethyl, β-phenoxyethyl, 3,4,5-trimethoxyphenyl, 2-furyl, 2-quinolyl, 2-phenyl-2H-1,2,3-triazol-4-yl and a moiety of the formula:

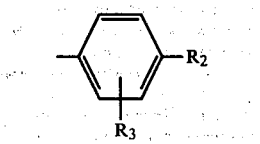

wherein $R_2$ is hydrogen, alkyl having up to 4 carbon atoms, fluoro, chloro, bromo, cyano, amino or dimethylamino and $R_3$ is hydrogen, methyl, fluoro, chloro, bromo or nitro; and the pharmacologically acceptable acid-addition salts thereof.

2. The compound according to claim 1, 1-(5-amino-4H-1,2,4-triazol-3-yl)-4-(p-methylbenzyl)piperazine.

3. The compound according to claim 1, 1-(5-amino-4H-1,2,4-triazol-3-yl)-4-(p-fluorobenzyl)piperazine.

4. The compound according to claim 1, 1-(5-amino-4H-1,2,4-triazol-3-yl)-4-phenethylpiperazine.

5. The compound according to claim 1, 1-(5-amino-4H-1,2,4-triazol-3-yl)-4-(cyclohexylmethyl)piperazine.

6. The compound according to claim 1, 1-(5-amino-4H-1,2,4-triazol-3-yl)-4-(o-fluorobenzyl)piperazine.

7. The compound according to claim 1, α-[4-(5-amino-4H-1,2,4-triazol-3-yl)-1-piperazinyl]-p-tolunitrile.

8. The compound according to claim 1, 2-[4-(5-amino-4H-1,2,4-triazol-3-yl)-1-piperazinylmethyl]-quinoline.

9. The compound according to claim 1, 1-(5-amino-4H-1,2,4-triazol-3-yl)-4-furfurylpiperazine.

10. The compound according to claim 1, 1-(5-amino-4H-1,2,4-triazol-3-yl)-4-(p-dimethylaminobenzyl)piperazine.

11. The compound according to claim 1, 1-(5-amino-4H-1,2,4-triazol-3-yl)-4-(3-phenylpropyl)piperazine.

12. The compound according to claim 1, 1-(5-amino-4H-1,2,4-triazol-3-yl)-4-(o-bromo-p-dimethylaminobenzyl)piperazine.

13. The compound according to claim 1, 1-(5-amino-4H-1,2,4-triazol-3-yl)-4-(m-chlorobenzyl)piperazine.

14. The compound according to claim 1, 1-(5-amino-4H-1,2,4-triazol-3-yl)-4-(m-chloro-p-dimethylaminobenzyl)piperazine.

15. The compound according to claim 1, 1-(5-amino-4H-1,2,4-triazol-3-yl)-4-(p-aminobenzyl)piperazine.

16. The compound according to claim 1, 1-(5-amino-4H-1,2,4-triazol-3-yl)-4-(o-methylbenzyl)piperazine.

17. The compound according to claim 1, 1-(5-amino-4H-1,2,4-triazol-3-yl)-4-(3,4,5-trimethoxybenzyl)piperazine.

18. The compound according to claim 1, 1-(5-amino-4H-1,2,4-triazol-3-yl)-4-(m-methylbenzyl)piperazine.

19. The compound according to claim 1, 1-(5-amino-4H-1,2,4-triazol-3-yl)-4-[(2-phenyl-2H-1,2,3-triazol-4-yl)methyl]piperazine.

20. The compound according to claim 1, 1-(5-amino-4H-1,2,4-triazol-3-yl)-4-(p-butylbenzyl)piperazine.

21. The compound according to claim 1, 1-(5-amino-4H-1,2,4-triazol-3)-yl-4-(p-tert.-butylbenzyl)piperazine.

22. The compound according to claim 1, 1-(5-amino-4H-1,2,4-triazol-3-yl)-4-(3-phenoxypropyl)piperazine.

23. The compound according to claim 1, 1-(5-amino-4H-1,2,4-triazol-3-yl)-4-(o-nitrobenzyl)piperazine.

24. The compound according to claim 1, 1-(5-amino-4H-1,2,4-triazol-3-yl)-4-(cyclopropylmethyl)piperazine.

25. The compound according to claim 1, 1-(5-amino-4H-1,2,4-triazol-3-yl)-4-benzylpiperazine.

26. A method of treating hypertension in a warm-blooded animal which comprises administering to said animal an effective amount of a compound selected from the group consisting of those of the formula:

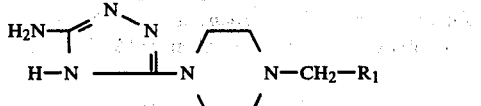

wherein $R_1$ is selected from the group consisting of alkyl having up to 3 carbon atoms, cycloalkyl having from 3 to 6 carbon atoms, allyl, benzyl, β-phenethyl, β-phenoxyethyl, 3,4,5-trimethoxyphenyl, 2-furyl, 2- quinolyl, 2-phenyl-2H-1,2,3-triazol-4-yl and a moiety of the formula:

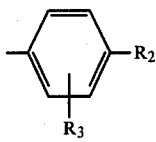

wherein $R_2$ is hydrogen, alkyl having up to 4 carbon atoms, fluoro, chloro, bromo, cyano, amino or dimethylamino and $R_3$ is hydrogen, methyl, fluoro, chloro, bromo or nitro; and the pharmacologically acceptable acid-addition salts thereof.

27. A composition of matter in dosage unit form comprising of the formula:

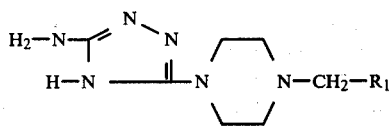

from about 5 mg. to about 200 mg. of a compound selected from the group consisting of those wherein $R_1$ is selected from the group consisting of alkyl having up to 3 carbon atoms, cycloalkyl having from 3 to 6 carbon atoms, allyl, benzyl, β-phenethyl, β-phenoxyethyl, 3,4,5-trimethoxyphenyl, 2-furyl, 2-quinolyl, 2-phenyl-2H-1,2,3-triazol-4-yl and a moiety of the formula:

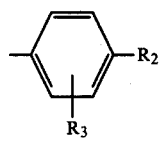

wherein $R_2$ is hydrogen, alkyl having up to 4 carbon atoms, fluoro, chloro, bromo, cyano, amino or dimethylamino and $R_3$ is hydrogen, methyl, fluoro, chloro, bromo or nitro; and the pharmacologically acceptable acid-addition salts thereof; in association with a pharmaceutically acceptable carrier.

28. A process for producing a compound of the formula:

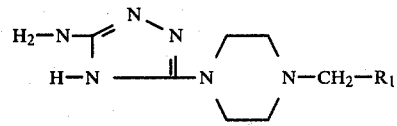

wherein $R_1$ is selected from the group consisting of alkyl having up to 3 carbon atoms, cycloalkyl having from 3 to 6 carbon atoms, allyl, benzyl, β-phenethyl, β-phenoxyethyl, 3,4,5-trimethoxyphenyl, 2-furyl, 2-quinolyl, 2-phenyl-2H-1,2,3-triazol-4-yl and a moiety of the formula:

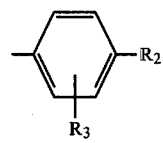

wherein $R_2$ is hydrogen, alkyl having up to 4 carbon atoms, fluoro, chloro, bromo, cyano, amino or dimethylamino and $R_3$ is hydrogen, methyl, fluoro, chloro, bromo or nitro; which comprises reacting dimethyl cyanodithiominocarbonate with a piperazine of the formula:

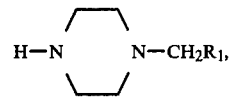

wherein $R_1$ is as described above, in ethanol at reflux for 4-18 hours, giving an N-cyano-4-substituted-1-piperazinecarboximidothioic acid, methyl ester of the formula

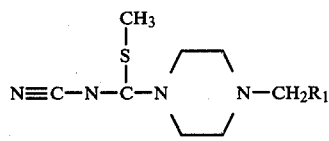

which is then reacted with hydrazine hydrate in ethanol at reflux.

29. A compound selected from the group consisting of 1-(5-amino-4H-1,2,4-triazol-3-yl)-4-(p-chloro-α-phenylbenzyl)piperazine and the pharmacologically acceptable acid-addition salts thereof.

30. A compound selected from the group consisting of 1-(5-amino-4H-1,2,4-triazol-3-yl)-4-cyclopentylpiperazine and the pharmacologically acceptable acid-addition salts thereof.

* * * * *